United States Patent [19]

Fischer et al.

[11] 4,393,060
[45] Jul. 12, 1983

[54] ISOCYANURIC ACID DERIVATIVES, METHOD OF PREPARATION, THERAPEUTIC COMPOSITIONS WITH A CYTOSTATIC ACTION AND THERAPEUTIC METHOD

[75] Inventors: Herbert Fischer; Manfred Budnowski; Ulrich Zeidler, all of Dusseldorf, Fed. Rep. of Germany

[73] Assignee: Henkel Kommanditgesellschaft auf Aktien, Dusseldorf-Holthausen, Fed. Rep. of Germany

[21] Appl. No.: 194,908

[22] Filed: Oct. 7, 1980

[30] Foreign Application Priority Data

Oct. 8, 1979 [AT] Austria ................................. 6552/79

[51] Int. Cl.$^3$ .................. A61K 31/53; A61K 31/535; C07D 251/32; C07D 413/08
[52] U.S. Cl. ........................... 424/248.5; 424/248.52; 424/248.55; 424/248.56; 424/248.57; 424/248.58; 424/249; 544/221; 544/113; 544/222
[58] Field of Search .................. 544/221, 113, 222; 424/249, 248.52, 248.57, 248.55, 248.56, 248.5, 248.58

[56] References Cited

U.S. PATENT DOCUMENTS

| | | | |
|---|---|---|---|
| 3,770,731 | 11/1973 | Jaeger | 544/221 |
| 3,779,949 | 12/1973 | Porret et al. | 544/221 |
| 3,910,908 | 10/1975 | Price | 544/221 |
| 3,914,225 | 10/1975 | Heistand et al. | 544/221 |
| 3,920,689 | 11/1975 | Jaeger | 544/221 |

FOREIGN PATENT DOCUMENTS

2132988  1/1972  Fed. Rep. of Germany ...... 544/221

OTHER PUBLICATIONS

Chemical Abstracts, vol. 90, 1979 #187948p.

*Primary Examiner*—John M. Ford
*Attorney, Agent, or Firm*—Hammond & Littell, Weissenberger and Muserlian

[57] ABSTRACT

N-substituted-diglycidyl-isocyanurates having the formula:

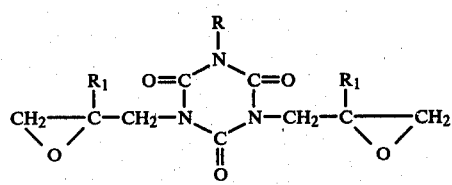

wherein R represents a hydrocarbon-containing radical selected from the group consisting of alkyl, aryl, aralkyl, alkaryl and cycloalkyl, optionally containing:
(a) heterocycles except epoxides, and unsaturation, and
(b) substituents selected from the group consisting of halogen, hydroxyl, amino, N-substituted amino, mercapto, alkylmercapto, arylmercapto, alkylsulfoxy, arylsulfoxy, alkoxy, aryloxy and acyloxy, and $R_1$ represents a member selected from the group consisting of hydrogen and alkyl having from 1 to 4 carbon atoms, as well as the method for preparing said N-substituted-diglycidyl-isocyanurates, therapeutic compositions with cytostatic action comprising said N-substituted-diglycidyl-isocyanurates, and a method of treatment of malignant neoplasias in warm-blooded animals by administering a therapeutically effective amount of said N-substituted-diglycidyl-isocyanurate.

10 Claims, No Drawings

ISOCYANURIC ACID DERIVATIVES, METHOD OF PREPARATION, THERAPEUTIC COMPOSITIONS WITH A CYTOSTATIC ACTION AND THERAPEUTIC METHOD

BACKGROUND OF THE INVENTION

The present invention relates to novel isocyanurates having two epoxy groups and the use of the same to treat malignant neoplasias and therapeutic compositions with a cytostatic action containing said isocyanurates having two epoxy groups.

It is known that a number of alkylating substances develop a cytostatic or cytotoxic effect. The best known compounds are derived from the so-called nitrogen mustards. Beyond that it is also known to use compounds containing at least two epoxy groups in the molecule as cancerostatic agents. Such compounds are, for instance, 4,4'-bis-(2,3-epoxypropyl)-di-piperidinyl-(1,1') and 1,2,-15,16-diepoxy-4,7,10,13-tetraoxohexadecane. However, these diepoxide compunds did not provide substantial improvement in cytostatic treatment and they are hardly used. They are utilized only occasionally for the treatment of brain tumors. The wider applicability of the above-mentioned compounds is also prevented by their limited solubility.

The subject matter of commonly assigned copending U.S. patent application Ser. No. 95,229, filed Nov. 19, 1979, now abandoned in favor of its continuation Ser. No. 257,893, filed Apr. 27, 1981, relates to therapeutic compositions having a cytostatic action which contain as the pharmacologically active ingredient triglycidyl isocyanurate (TGI) and/or such TGI derivatives where the hydrogen atom attached to the carbon in the 2 position of one or more of the glycidyl groups is replaced by an alkyl having from 1 to 4 carbn atoms. Compounds of this kind are characterized by the three nitrogen atoms of the isocyanuric acid ring being substituted by glycidyl groups containing epoxy-groups, which can also be substituted in the 2 position with an alkyl having from 1 to 4 carbon atoms.

OBJECTS OF THE INVENTION

An object of the present invention is the development of novel isocyanurates having two epoxy groups which have a cytostatic action.

Another object of the present invention is the development of N-substituted-diglycidyl-isocyanurates having the formula:

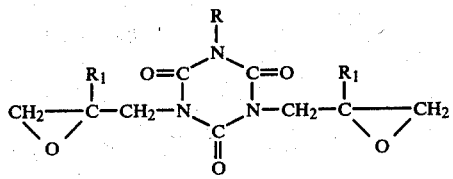

wherein R represents a hydrocarbon-containing radical selected from the group consisting of alkyl, aryl, aralkyl, alkaryl and cycloalkyl, optionally containing:
(a) heterocycles except epoxides, unsaturation, and
(b) substituents selected from the group consisting of halogen, hydroxyl, amino, N-substituted amino, mercapto, alkylmercapto, arylmercapto, alkylsulfoxy, arylsulfoxy, alkoxy, aryloxy and acyloxy,
and $R_1$ represents a member selected from the group consisting of hydrogen and alkyl having from 1 to 4 carbon atoms.

A further object of the present invention is the development of a method for the preparation of the above N-substituted-diglycidyl-isocyanurates.

A still further object of the present invention is the obtaining of a therapeutic composition with a cytostatic action consisting essentially of a therapeutically effective amount—preferably being in the range of from 0.05% to 5% by weight—of at least one N-substituted-diglycidyl-isocyanurate having the formula:

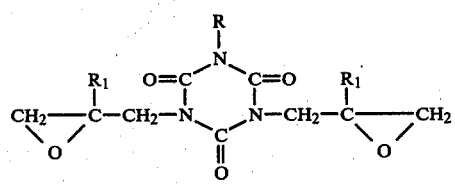

wherein R represents a hydrocarbon-containing radical selected from the group consisting of alkyl, aryl, aralkyl, alkaryl and cycloalkyl, optionally containing:
(a) heterocycles except epoxides, unsaturation, and
(b) substituents selected from the group consisting of halogen, hydroxyl, amino, N-substituted amino, mercapto, alkylmercapto, arylmercapto, alkylsulfoxy, arylsulfoxy, alkoxy, aryloxy and acyloxy,
and $R_1$ represents a member selected from the group consisting of hydrogen and alkyl having from 1 to 4 carbon atoms, the remainder being conventional pharmaceutical vehicles.

A yet further object of the present invention is the development of a method for the treatment of malignant neoplasias in warm-blooded animals comprising administering a cytostatically effective amount of at least one N-substituted-diglycidyl-isocyanurate having the formula:

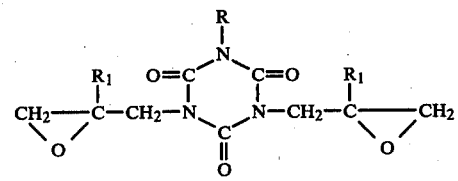

wherein R represents a hydrocarbon-containing radical selected from the group consisting of alkyl, aryl, aralkyl, alkaryl and cycloalkyl, optionally containing:
(a) heterocycles except epoxides, unsaturation, and
(b) substituents selected from the group consisting of halogen, hydroxyl, amino, N-substituted amino, mercapto, alkylmercapto, arylmercapto, alkylsulfoxy, arylsulfoxy, alkoxy, aryloxy and acyloxy.
and $R_1$ represents a member selected from the group consisting of hydrogen and alkyl having from 1 to 4 carbon atoms, to a warm-blooded animal suffering from a malignant neoplasia.

These and other objects of the invention will become more apparent as the description thereof proceeds.

DESCRIPTION OF THE INVENTION

The present invention results from the observation that compounds which are structurally analogous to triglycidyl-isocyanurate, which have, however, only two glycidyl groups attached to two of the nitrogen atoms and the further nitrogen atom is substituted by certain select substituents, also develop a surprisingly strong cytostatic effectiveness, which can even exceed that of TGI.

Accordingly, subject matter of the present invention are medicinal preparations with cytostatic efficacy, containing compounds of the general formula (I):

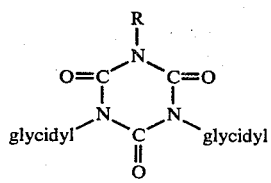

wherein R has the following meanings: alkyl aryl, aralkyl, alkaryl, cycloalkyl, which substituents can optionally be of heterocyclic character and/or unsaturated and/or can be substituted with at least one of the following substituents: halogen, hydroxyl, amino, N-substituted amino, mercapto, alkylmercapto, arylmercapto, alkylsulfoxy, arylsulfoxy, alkoxy, aryloxy, acyloxy and a heterocyclic group. Glycidyl corresponds to the general formula (II):

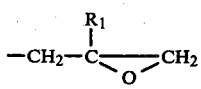

where, in formula II, $R_1$ is preferably hydrogen but can also represent lower alkyl having from 1 to 4 carbon atoms.

More particularly, the present invention involves:

(A) N-substituted-diglycidyl-isocyanurates having the formula:

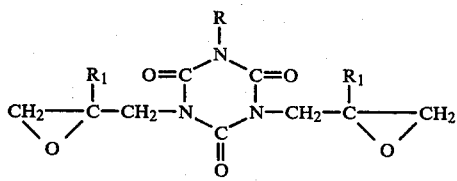

wherein R represents a hydrocarbon-containing radical selected from the group consisting of alkyl, aryl, aralkyl, alkaryl and cycloalkyl, optionally containing:
(a) heterocycles except epoxides, unsaturation, and
(b) substituents selected from the group consisting of halogen, hydroxyl, amino, N-substituted amino, mercapto, alkylmercapto, arylmercapto, alkylsulfoxy, arylsulfoxy, alkoxy, aryloxy and acyloxy.
and $R_1$ represents a member selected from the group consisting of hydrogen and alkyl having from 1 to 4 carbon atoms.

(B) A therapeutic composition with a cytostatic action consisting essentially of a therapeutically effective amount of at least one N-substituted-diglycidyl-isocyanurate having the formula:

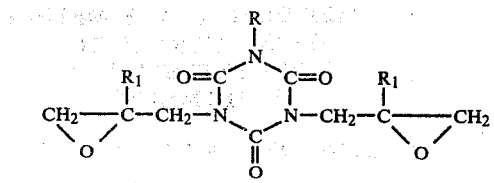

wherein R represents a hydrocarbon-containing radical selected from the group consisting of alkyl, aryl, aralkyl, alkaryl and cycloalkyl, optionally containing:
(a) heterocycles except epoxides, unsaturation, and
(b) substituents selected from the group consisting of halogen, hydroxy, amino, N-substituted amino, mercapto, alkylmercapto, arylmercapto, alkylsulfoxy, arylsulfoxy, alkoxy, aryloxy and acyloxy,
and $R_1$ represents a member selected from the group consisting of hydrogen and alkyl having from 1 to 4 carbon atoms, the remainder being conventional pharmaceutical vehicles.

(C) A method for the treatment of malignant neoplasias in warm-blooded animals comprising administering a cytostatically effective amount of at least one N-substituted-diglycidyl-isocyanurate having the formula:

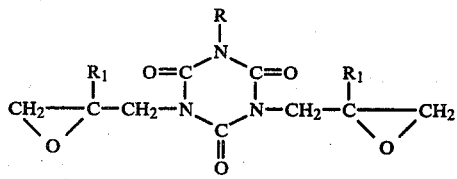

wherein R represents a hydrocarbon-containing radical selected from the group consisting of alkyl, aryl, aralkyl, alkaryl and cycloalkyl, optionally containing:
(a) heterocycles except epoxides, unsaturation, and
(b) substituents selected from the group consisting of halogen, hydroxyl, amino, N-substituted amino, mercapto, alkylmercapto, arylmercapto, alkylsulfoxy, arylsulfoxy, alkoxy, aryloxy and acyloxy,
and $R_1$ represents a member selected from the group consisting of hydrogen and alkyl having from 1 to 4 carbon atoms, to a warm-blooded animal suffering from a malignant neoplasia.

In compounds of the general formula I, R is preferably a substituted alkyl, more particularly, a substituted alkyl derived from a reaction with an epoxide group. The unsaturated substituents are preferably olefinically unsaturated substituents, particularly mono-olefinically unsaturated substituents, such as alkenyl, having from 2 to 18 carbon atoms.

The working mechanism of the compounds utilized within the scope of the invention has not been determined in detail. It is thought, however, that the glycidyl groups, here as in the triglycidyl isocyanurate of Ser. No. 95,229, are of extraordinary significance with respect to the cytostatic efficacy of the compounds.

All compounds of general formula described for this invention are characterized by the presence of two such glycidyl groups. In addition, there is the widely variable substituent R present in the respective class of compounds. It is possible that via this substituent R, influence is exerted upon the distribution of lipophilic and hydrophilic properties of the molecule and that with small changes of the lipophilic/hydrophilic balance, the uptake of the compounds by the organism can be controlled. However, the significance of substituent R introduced by this invention is not necessarily restricted to the above theory.

According to the above-stated definition, the substituent R is a hydrocarbon radical, which can also contain hetero-atoms or be substituted. When hetero-atoms are present these are primarily N, O and/or S. Preferably each of these substituents R contains no more than 15 carbon atoms, ideally no more than 12 carbon atoms and especially suitably no more than 8 carbon atoms. Of particular interest are especially substituents R which contain up to 6 or preferably only up to 4 carbon atoms, whereby these numerical values are to be understood to be independent of the respective structure and only refer to the sum of all carbon atoms in the respective substituent.

If R is an aryl, aralkyl or alkaryl substituent, where aryl represents a hydrocarbon aryl, then particularly single ring substituents are preferred. Phenyl, benzyl, tolyl, xylyl and related compounds are typical representatives. Also where the substituent R is cycloaliphatic, single ring systems on the basis of cyclopentyl, cyclohexyl and their derivatives are preferred. Correspondingly, of the heterocyclic substituents, thus especially single ring cyclic compounds with O, N and/or S in the system fall within the frame of the invention. These ring systems can thus preferentially contain 1, 2 or 3 such hetero-atoms. These heterocyclic substituents contain preferentially 5 or 6 ring elements. If desired, all ring substitutes mentioned above, be they of aromatic or cycloaliphatic nature, can themselves contain further substitutes. Suitable substitutes are, for instance, halogen, hydroxyl or alkoxy.

In an especially preferred version of the invention, substituent R means an optionally substituted alkyl. This alkyl can be a straight chain or be branched or also alkenyl and contain, not counting substituents, preferably not more than 10, especially not more than 8, carbon atoms. In this version of the invention, there are especially preferred those compounds of general formula I where the substituent R is a non-substituted alkyl with 1 to 6 carbon atoms or a corresponding alkyl which is substituted with halogen, hydroxyl, amino, N-substituted amino, mercapto, alkylmercapto, hydrocarbon arylmercapto, alkylsulfoxy, hydrocarbon arylsulfoxy, alkoxy, hydrocarbon aryloxy and/or acyloxy, or the substitute can also be of heterocyclic nature.

Such substituted substituents R can also be substituted once or repeatedly with the mentioned groups. Preferentially 1 to 3 of the mentioned substitutes are located on the respective substituent R, whereby in a particularly preferred case such substituted alkyl of the mentioned type, contained in compounds of general formula I, are used as per this invention in the preparation of medications.

Most preferably the substituent R, a substituted alkyl, has the formula:

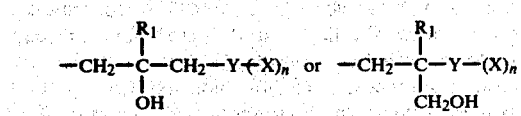

where Y is O, N, S, SO$_2$ or P; X is H, hydroxyl, halogen, lower alkyl, lower alkylol, hydrocarbon aryl and lower alkanoyl; n is an integer of the valence of Y minus 1, and R$_1$ has the above-assigned values.

When substituted groups are located on the substituted alkyl group, which in turn contain hydrocarbons, thus particularly in the case of N-substituted amino, alkylmercapto, arylmercapto, alkylsulfoxy, arylsulfoxy, alkoxy, aroxy and acyloxy, these substituting groups have preferentially not more than 10, ideally not more than 8, carbon atoms. The especially preferred limit lies at 6 carbon atoms, particularly at no more than 4 carbon atoms. These substituting hydrocarbon groups can themselves be aryl, aralkyl, alkaryl, cycloalkyl and/or alkyl which, optionally, can also be substituted by such substituents as halogen, hydroxyl, alkoxy and the like.

Here also hetero-atoms containing substituents of the above-mentioned type can be present, thus, for example, heterocyclic ring systems with 1 to 3 heteroatoms of the above-mentioned type, especially single rings with N, O and/or S as hetero-atoms. Corresponding 5- or 6-membered heterocycles, respectively, are preferred.

In a particularly preferred version compounds of general formula I are used, where the substituent R is a monosubstituent or disubstituted alkyl of the mentioned type, which is selected from the following group: monohydroxyalkyl, dihydroxyalkyl, halo-hydroxyalkyl, N-substituted aminohydroxyalkyl, alkylmercaptohydroxyalkyl, substituted alkylmercapto-hydroxyalkyl, the corresponding alkylsulfoxy-hydroxyalkyls, optionally substituted alkoxy-hydroxyalkyl and optionally substituted acyloxy-hydroxyalkyl. Preferably the alkyl has up to 7, preferably 3 to 7 and in particular 3, 4 or 5, carbon atoms.

Within the scope of this invention, compounds of general formula I can be employed where the substituent R signifies a straight-chained or branched unsubstituted alkyl with up to 6, preferably up to 4, carbon atoms. These unsubstituted alkyls are particularly methyl, ethyl, propyl, isopropyl as well as the corresponding C$_4$-remnants and their monoolefinically unsaturated analogs, such as alkenyls having up to 4 carbon atoms, especially allyl.

Furthermore, especially those compounds of general formula I are preferred where the substituent R is a monosubstituted or disubstituted alkyl of the mentioned type, with 3 carbon atoms and also preferentially has at least one hydroxyl group. Thus, at least one hydroxy group is always present, preferably in addition to a further substituent in the propyl chain.

These substituting groups distribute themselves, in a further preferred version of the invention, into the 2 and the 3 position of the affected substituent R. Thereby the hydroxy group can be located either in the 2 position or the 3 position. Furthermore especially preferred are correspondingly substituted compounds of formula I, which show substituent R, as having apart from the hydroxyl group, no other substituting group or as further substitutes hydroxyl, halogen, an N-substituted amino, a possibly substituted alkoxy, a possibly substituted alkylmercapto, or alkylsulfoxy or a possibly substituted acyloxy. Chlorine and/or bromine are preferred as halogens; however, fluorine and iodine are not excluded. The N-substituted amino remnants can correspond to the formula:

Here the R$_2$ and R$_3$, respectively, are hydrocarbon radicals, which in turn can be substituted. In the preferred version of the invention, $R_2$ and, where present, $R_3$ contain up to 12 carbon atoms; where the carbon atoms of the disubstitution at the nitrogen of $R_2$ and $R_3$ is not to exceed the sum of 12 carbon atoms. The substituents $R_2$ and $R_3$ contain preferentially a total of up to 8 and particularly not more than 5 carbon atoms. The substituents $R_2$ and $R_3$ can also be joined into a saturated or unsaturated, possibly aromatic and/or heterocyclic ring. Specifically, $R_2$ and $R_3$ when taken together can be alkylene, alkylazaalkylene and alkoxyalkylene. Preferentially $R_2$ and possibly $R_3$ are alkyl. If these alkyls are in turn substituted again, then within the scope of the invention such substituents as particularly hydroxyl, alkoxy and halogen, preferably chlorine or bromine, are desired.

If the substituent R contains a substituted hydroxy group, such as acyloxy, alkoxy, alkylmercapto or alkylsulfoxy this substituent preferentially contains also maximally up to 10 carbon atoms, whereby here also the preferred limit is 8 carbon atoms and it is ideally preferred to introduce not more than 5 carbon atoms into the molecule at this site. Preferably the acyloxy is alkanoyloxy with the necessary number of carbon atoms, although aroyloxy, such as benzoyloxy is not excluded. The acyloxys are preferentially derived from alkanoic acids of the mentioned carbon number.

The medicinal preparations according to the invention can contain preferably individual, defined compounds of general formula I. However, it has been shown that ingredient mixtures of several compounds under the general formula I are highly effective cytostatica. The medicinal preparations preferably contain from 0.05% to 5% by weight of at least one compound of the general formula I, and the remainder to 100% conventional inert aqueous pharmaceutical vehicles. Within the scope of the invention it is further preferred to utilize specific individual compounds or a mixture of several compounds as per definition for this invention according to formula I, in blends with TGI compounds according to Ser. No. 95,229. In this event, the total amount of cytostatically active ingredients in the medicinal preparations can be the same as above.

The preparation of active ingredients of formula I is a further objective of the invention. Basically the reaction mechanisms are known and the following possibilities of reaction exist.

Triglycidyl isocyanurate can be reacted with a deficiency of water, alcohol, primary and/or secondary amines, mercaptans, imines, imides, carboxylic acids, hydrohalic acids and the like, or hydrogen. On the basis of the equivalence of the three glycidyl groups in TGI, this reaction leads initially always to product mixtures, which by themselves can be therapeutically effective. But it is also possible, and part of the following described procedure of the invention, to separate out from these mixtures the corresponding compounds of general formula I, through suitable separating procedures, for instance, through preparative thin-layer chromatography or column chromatography.

Within the scope of this reaction, one glycidyl group is converted into the substituent R of the compounds of the general formula I.

During the reduction treatment of the glycidyl group with hydrogen or with hydrogen-producing compounds, a monohydroxyalkyl substituent R is produced. The hydrogen-producing compounds which can be used are, for instance, hydride compounds, such as complex boron hydrides, for example, sodium borohydride. In the other cases mentioned, the original triglycidyl compound is reacted with a nucleophilic compound $H^{\oplus}A^{\ominus}$ in a deficient system, whereby a disubstituted substituent R is produced which contains, apart from a hydroxyl group, the substituent $A^{\ominus}$ as a second substituent, normally at the adjacent carbon atom to the hydroxylized carbon atom.

Basically the reaction of glycidyl groups of the TGI with such nucleophilic reaction partners is a known state of technology and has, for instance, been described in Angew. Chemie 80, 851 (1968). However, within the current technology this reaction is made deliberately on more than one epoxide group of the TGI and serves, for instance, in an industrial situation to establish crosslinking in epoxide resin systems. In the method according to this invention, procedural conditions are preferentially selected which enable a far-reaching increase in the yield, in the direction of 1:1 of the reaction products, as well as the subsequent isolation and extraction of these 1:1 reaction products, with the separation of unreacted constituents of the original material and usable reaction product, which was obtained through the reaction of more than one epoxide group with the nucleophilic reaction partner. For the reaction of TGI compounds with nucleophilic reaction partners $H^{\oplus}A^{\ominus}$ of the above-mentioned type, it can be difficult to obtain the desired 1:1 reaction products in the preferred yield, since the three epoxide groups of the molecule of the original compound are about identical in the reaction, and thus the desired diglycidyl compound is frequently not formed as the preferred reaction product.

The attempt to enrich the desired compound by reacting the triglycidyl isocyanurate with a deficiency of the nucleophilic reaction partner is only feasible in few cases, because there occurs in many cases a very slight polymerization of the triglycidyl isocyanurate.

The extraction of the 1:1 reaction products succeeds relatively easy, as a rule, only when mercaptans, amines and hydrides are selected as reactants. Hereby one can obtain partial epoxide ring opening products of the desired constitution, with starting mixtures which contain the reactants in a ratio of 1:1 or with only a slight excess of one of the reactants. More difficult is the extraction of the corresponding reaction products of TGI when, for instance, carboxylic acids, water or alcohols are employed.

It was found that the preparation of the 1:1 reaction product becomes surprisingly simple when one reacts triglycidyl isocyanurate with an excess, and preferably with a large excess, of the nucleophilic reactant $H^{\oplus}A^{\ominus}$, terminates the reaction prematurely and then separates the excess of nucleophilic reaction partner, the unused TGI and the also formed di- and tri-addition products. The remaining raw diglycidyl product can then in a conventional manner, for instance through column chromatography, be purified. In this process the nucleophilic reaction partner is used in a 3 to 30 fold excess, especially in a 5 to 20 fold excess of the required amount, 1:1 molar ratio. The reaction can be conducted in solvents and, if possible, the excess of nucleophilic reaction partner can serve as a solvent. If solvents are being used, these should be suitably polar but not reactive under the selected operating conditions. Preferably the solvent is not water miscible. Through the selection of a proper solvent, the polymerizing tendency of TGI is suppressed and side reactions, through the addition of solvent to the epoxide group, is avoided. In addition, the working up of the reaction mixture through the separation of the reactants and the undesired reaction products can be facilitated by proper solvent selection. Especially suitable solvents are, for example, halogenated hydrocarbons, particularly chlorinated hydrocarbons. The reaction is commonly conducted at temperatures between about 30° C. and 120° C., preferably 40° C. to 100° C. The reaction temperature is selected in a particularly suited version, so that within four to five hours the epoxide content of the reaction mixture has been reduced to one half.

By the selection of proper reaction parameters, the purification of the reaction raw product is frequently possible in a very simple manner. The excess of the nucleophilic reaction partner, part of the monoglycidyl compound, as well as the component of the reaction product wherein all three epoxide groups are reacted, can frequently be removed by extraction of the organic phase with water. The solvent is evaporated from the residual reaction mixture. On taking up the residual reaction mixture in methanol, the unreacted TGI remains undissolved and can be separated. Finally, after evaporation of the methanol, only the raw diglycidyl compound (1:1 reaction product) remains, which can be purified through simple fractionation, for instance, by column chromatography. Silica gel can be utilized as the separating agent. The eluant may, for example, be methylene chloride/ethyl acetate or methylene chloride/acetone. Purification and extraction of the two epoxide groups containing 1:1 reaction product from the mixture of reactants is, here and in the other methods described below, as a rule, an essential step in the process as per the invention. For the manufacture of sulfoxy compounds from the corresponding mercapto compounds, see Houben-Weyl aaO, Vol. 9, 207-217 (1955), as well as Makrol. Chem. 169, 323 (1979).

A rather elegant general method for the preparation of compounds from general formula I is based on the reaction of mono-N-substituted isocyanuric acid with epihalohydrins. The preparation of mono-N-substituted isocyanuric acids can be made with known published methods. For the relevant literature one is, for instance, referred to W. J. Close, J. Am. Chem. Soc. 75, 3617 (1953). This source describes apart from older relevant works, a generally applicable process where mono-substituted biuret compounds are reacted with alkyl carbonates, especially ethyl carbonate, in the presence of an alkali metal alkoxide, especially sodium ethoxide, to produce a mono-N-substituted isocyanuric acid. The substitute introduced by this process corresponds, as a rule, to substituent R in compounds of general formula I.

In a follow-up reaction the two glycidyl groups are then introduced. For this purpose, the mono-N-substituted isocyanuric acid is reacted with the required epihalohydrin compound, for instance, with epichlorohydrin. This reaction also takes place in the known manner. It can be made in the presence of a small amount of a quarternary ammonium compound as catalyst. (For this, see for instance, Houben-Weyl, Methoden der organischen Chemie, Vol. 14/2, 497, 547 [1963].)

In a modification of this reaction mechanism, the mono-N-substituted isocyanuric acid is not directly reacted with the epoxide compound. Instead, initially it is reacted with an allyl halide to give a diallyl substituted compound which corresponds to the diglycide compounds belonging to formula I. However, instead of the epoxide group, they have an olefinic double bond. The then prepared diallyl-substituted isocyanurates are then epoxidized on the double bond. The epoxidation is accomplished according to established procedures with peracids. For instance, the reaction of cyanuric acid with an allyl halide is described in U.S. Pat. No. 3,376,301. The epoxidation of allyl isocyanurates with peracids is, for instance, described in Houben-Weyl aaO, Vol. 6/3, 385 ff. It can, for instance, be accomplished in the presence of a small amount of a quarternary ammonium compound as catalyst.

The reaction of the mono-N-substituted isocyanuric acid with epihalohydrins and allyl halides, respectively, occurs suitably in the temperature range from about 50° C. to 150° C., preferably from about 70° C. to 125° C.

Allyl halide and epihalohydrin are utilized at a mol ratio of at least 2:1 of the isocyanuric acid compound. However, a substantial excess, for instance, up to a mol ratio of 10:1 can be employed. Operating with mol ratios in the area from 2 to 4 mols of allyl halide or epihalohydrin, respectively per mol of isocyanuric acid compound can be particularly useful. The preferred allyl halide or epihalohydrin, respectively, contain chlorine or possibly bromine as halogens.

The reaction can be conducted in polar aprotic solvents, which dissolve one reaction partner at least partially and which are inert to the reactants. A particularly useful solvent medium is the class of dialkylformamides, especially the lower dialkylformamides, such as dimethylformamide. The mono-N-substituted isocyanuric acid compound can be utilized as such or as a salt. The preferred reaction time is one to ten hours, particularly two to five hours.

The epoxidation of the allyl groups by means of peracids is also preferably conducted in the presence of solvents. Suitable are polar solvents, such as, for example, halogenated carbons or alcohols. The suitable reaction temperature is customarily in the range from 0° to 50° C., especially between 10° C. to 30° C. The peracid is utilized ideally in an approximately equivalent amount or in only slight excess. m-Chloroperbenzoic acid is easily accessible as a commercial product and it is suited for accomplishing the reaction. The reaction time is, as a rule, in the area of 24 hours or more, for instance, up to 48 hours.

A further object of the present invention is the development of a process for the preparation of N-substituted diglycidyl-isocyanuric acid compounds of general formula I:

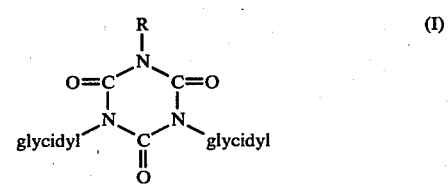

where R represents alkyl, aryl, aralkyl, alkaryl or cycloalkyl, which can, if desired, be of heterocyclic nature and/or unsaturated and/or be substituted with one of the following substituents: halogen, hydroxyl, amino, N-substituted amino, mercapto, alkylmercapto, arylmercapto, alkylsulfoxy, arylsulfoxy, alkoxy, aryloxy, acyloxy and heterocycles, and glycidyl represents a group of the general formula II:

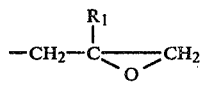

$$-CH_2-\underset{R_1}{\overset{}{C}}\underset{O}{\overset{}{\diagdown}}CH_2 \quad (II)$$

wherein $R_1$ represents hydrogen preferably, but also a lower alkyl with 1 to 4 carbon atoms. This process is characterized in that:

(A) the two glycidyl groups are introduced into the mono-N-substituted isocyanuric acid substituted with substituent R to give a product of general formula II, or (B) a triglycidyl isocyanuric acid with glycidyl remnants of general formula II is subjected to a partial reaction with water, alcohols, compounds with a primary or secondary amino group, mercaptans, hydrogen sulfide, carboxylic acids, hydrohalic acids or hydrogen or compounds giving off hydrogen, optionally the thusformed mercapto compounds are converted to the respective sulfoxy compounds, and the formed reaction products of general formula I are recovered from the reaction mixture.

If in this procedure the two glycidyl groups of general formula II are introduced into mono-N-substituted isocyanuric acid, this can be accomplished in such a manner by either reacting mono-N-substituted isocyanuric acid containing substituent R with an epihalohydrin, whereby the epihalohydrin compound corresponds to the glycidyl group of formula II, or initially reacting the mono-N-substituted isocyanuric acid with the corresponding allyl halide, followed by epoxidation, preferably with peracids, of the allyl group or with the $R_1$ substituted allyl group, respectively, to convert the same to the glycidyl group.

The compounds of general formula I in purified and extracted form are new compounds. As such, particularly in isolated form suitable for the use as medication, they fall into the scope of the invention presented here. For this aspect of the invention all previously mentioned general details in regard to the definition of compounds of general formula I with their substituents R and glycidyl are also applicable. Budnowski, Angewandte Chemie 80, 851 (1968), formulates, as an intermediate step in the reaction of a large excess of epichlorohydrin with cyanuric acid, a reaction product that apart from two epoxide groups substituted on nitrogen atoms has a 2-hydroxy-3-chloropropyl substituent on the nitrogen atom. It was mentioned that this intermediate product had been determined by means of thinlayer chromatography. However, the isolation of this compound as a substance is not described in this literature source, and its process of production is unrelated to the above-described processes.

Finally an object of the invention is also the use of compounds of general formula I for the treatment of malignant neoplasias, including a reduction in the number of P388 (Leukemia) tumor type cells in mice. Individual doses of the compounds at levels from 1 to 200 mg/kg are suitable. Individual, specific compounds of general formula I can be used singly or as mixtures. Also their use as mixtures with TGI falls into the scope of this invention. Compounds used as per the invention according to general formula I occur in various stereoisomeric forms. Basically all of these various forms are suitable for the purposes of the invention. They can be utilized in mixtures or also in the form of specifically isolated isomers.

For utilization as cancerostatica the active ingredients should be applied by means of suitable vehicles. For that purpose the common pharmaceutical excipients for pharmacological preparations are suitable. For the case presented here, the use of aqueous systems, possibly together with compatible glycolethers, such as ethylene glycol monoethylether or butylene glycol methylether or propylene glycol methylether have shown to be reliable, especially when the effective ingredient is to be applied parenterally. For oral application the usual pharmaceutical excipients are usable, as long as they have a corresponding compatability with the glycidyl compounds.

In animal experiments the utilization of freshly prepared, aqueous solutions, which were given i.p. or i.v., has proven to be useful. Compounds used as per the invention are effective against various forms of leukemia as well as malignant neoplasms, such as lung carcinoma, colon carcinoma, melanoma, ependymoblastoma and sarcoma. It has been shown that in some cases a clear superiority over cyclophosphamide and fluoruracil were found.

A combination therapy in connection with other cytostatica, such as derivatives of nitrogen mustards or even fluoruracil, is possible.

Very generally, in the scope of the invention, it is preferable that the compounds of general formula I with substituent R, that are employed, are those where the substituent R, at least under normal conditions, should display no substantial reactivity, or none at all with the epoxide group of the glycidyl substitute or substitutes on the ring system of general formula I. This assures that the active ingredients used as per the invention have a sufficiently long storage life and that undesirable reactions, causing destruction of the epoxide group do not occur. This prerequisite has to be kept in mind, especially also for the selection of possibly substituents R.

Examples of substituent R in compounds of general formula I with cytostatic effectiveness used as per the invention are the following: alkyl having from 1 to 8 carbon atoms, such as methyl, ethyl, propyl, butyl, pentyl, hexyl; the corresponding isomers, such as isopropyl, isobutyl, tert.-butyl, isopentyl; corresponding unsaturated, especially olefinic unsaturated radicals, for example, alkenyl having from 2 to 8 carbon atoms, such as vinyl, allyl, butenyl; aryl hydrocarbon having from 6 to 12 carbon atoms, such as phenyl, benzyl, xylyl, trimethylphenyl, isopropylphenyl, naphthyl; cycloalkyl having from 5 to 12 carbon atoms, such as cyclopentyl, cyclohexyl; the corresponding substituted cycloalkyls with 1 to 3 alkyls or alkenyls, respectively, whereby the alkyl or alkenyl substituents, respectively, have preferentially 1 to 4 carbon atoms;
2,3-dihydroxypropyl
2-hydroxy-3-diethylamino-propyl
2-hydroxy-3-dimethylamino-propyl
2-hydroxy-3-(dihydroxyethylamino)-propyl
2-hydroxy-3-morpholino-propyl
2-hydroxy-3-phenoxy-propyl
2-hydroxy-3-methoxy-propyl
2-hydroxy-3-ethoxy-propyl
2-hydroxy-3-propoxy-propyl
2-hydroxy-3-acetoxy-propyl
2-hydroxy-3-propyloxy-propyl
2-hydroxy-3-butyloxy-propyl
2-hydroxy-3-(3-carboxypropyloxy)-propyl
3-hydroxy-2-acetoxy-propyl
3-hydroxy-2-butyloxy-propyl 3-hydroxy-2-(3-carboxypropyloxy)-propyl
2-hydroxy-3-chloro-propyl, and
2-hydroxy-3-bromo-propyl.

Additional examples, in the scope of the invention, for R are the following:
haloalkyl
hydroxy-alkylthiopropyl
2-hydroxy-3-methylaminopropyl
2-hydroxy-3-ethylaminopropyl
2-hydroxy-3-di($\beta$-chlorethyl)amino-propyl
2-hydroxy-3-benzyloxy-propyl, and
2-hydroxy-3-hydroxypropyloxy-propyl.

Further possibilities for the substituent R are:
2-hydroxy-3-methylthio-propyl
2-hydroxy-3-butylthio-propyl
2-hydroxy-3-phenylthio-propyl
2-hydroxy-3-(benzoxazol-2'-ylthio)-propyl
2-hydroxy-3-acetylthio-propyl
2-hydroxy-3-octylthio-propyl
2-hydroxy-3(2',3'-dihydroxy-propylthio)-propyl
2-hydroxy-3-(benzimidazol-2'-ylthio)-propyl, and
2-hydroxy-3-(benzthiazol-2'-ylthio)-propyl.

Reactants for the reaction with a glycidyl group of triglycidyl isocyanurate resulting in the formation of a substituted R substituent, within the scope of the invention, are very generally alkanols having from 1 to 8 carbon atoms, such as methanol, ethanol, n-propanol, isopropanol, n-butanol, isobutanol, sec.-butanol, tert.-butanol, 1-pentanol, 2-pentanol, 3-pentanol, 2-methyl-1-butanol, 3-methyl-1-butanol, 2-ethyl-2-butanol, 3-methyl-2-butanol, 2,2-dimethyl-1-propanol, 1-hexanol, 2-ethyl-1-butanol, 4-methyl-1-pentanol, 4-methyl-2-pentanol, and 2-methyl-1-pentanol.

As unsaturated alcohols one can, for instance, utilize alkenols and alkynols having from 3 to 8 carbon atoms, such as 2-buten-1-ol, 2-propyn-1-ol, allyl alcohol, crotyl alcohol, 3-buten-2-ol, 2-buten-1-ol and 3-butyn-2-ol.

Examples of polyhydric alcohols are particularly alkanepolyols, alkenepolyols and alkynepolyols having 2 to 8 carbon atoms and 2 to 4 hydroxyl groups, such as:
ethylene glycol
propanediol-1,2
propane-diol-1,3
butanediol-1,4
butanediol-1,2
butanediol-2,3
butanediol-1,3
2-butenediol-1,4
2-butyne-1,4-diol
1,5-pentanediol
2-methyl-1,4-butanediol
2,2-dimethyl-1,3-propanediol
hexanediol
2,5-dimethyl-3-hexyne-2,5-diol
glycerine
1,2,4-butanetriol
2-hydroxymethyl-2-ethyl-propanediol
2-methyl-2-hydroxymethyl-1,3-propanediol, and
pentaerythritol.

Examples of thiols are in this context alkanethiols and alkanedithiols having from 1 to 8 carbon atoms, such as:
methanethiol
ethanethiol
1-propanethiol
2-propanethiol
2-methyl-2-propanethiol
2-butanethiol
2-methyl-1-propanethiol 1-butanethiol
1-pentanethiol
1-hexanethiol, as well as:
1,2-ethanedithiol
2,2-propanedithiol, also aromatic thiols such as:
benzenethiol
p-benzene-dithiol
pyridine-2-thiol, and
thiophen-2-thiol.

The sulfoxide compounds obtained from such mercapto substituents are within the scope of this invention. Examples of carboxylic acids are especially alkanoic acids having 2 to 12 carbon atoms, such as acetic acid, propionic acid, n-butyric acid, n-valeric acid, capric acid, enanthic acid, isobutyric acid, 3-methylbutanoic acid, 2,2-dimethylpropanoic acid, 2-methyl-butanoic acid, 2-ethylbutanoic acid, 2-ethylhexanoic acid.

Unsaturated acids are, for instance, alkenoic acids, alkynoic acids and alkadienoic acids having from 3 to 12 carbon atoms, such as propenoic acid, 2-methylpropenoic acid, 3-methylpropenoic acid, 2,3-dimethylpropenoic acid, hexadienoic acid, and propiolic acid.

Examples of substituted acids are especially haloalkanoic acids having from 2 to 12 carbon atoms and 1 to 5 halogens, such as:
2-chloropropanoic acid
3-chloropropanoic acid
2,2-dichloropropanoic acid
2,3-dichloropropanoic acid
3,3-dichloropropanoic acid
2,2,3,3,3-pentachloropropanoic acid
2-chlorobutanoic acid
3-chlorobutanoic acid
4-chlorobutanoic acid
2-chloro-2-methyl-propanoic acid
3-chloro-2-methyl-propanoic acid
2,3-dichlorobutanoic acid
2,2,3-trichlorobutanoic acid
2-chloropentanoic acid
3-chloropentanoic acid
4-chloropentanoic acid
5-chloropentanoic acid
2-chloro-2-methyl-butanoic acid
2-chloro-3-methyl-butanoic acid, and
3-chloro-2,2-dimethyl-propanoic acid.

Examples of aromatic acids are especially aromatic hydrocarbon carboxylic acids having from 7 to 12 carbon atoms and 1 to 6 carboxyl groups, such as benzoic acid, phthalic acid, isophthalic acid, terephthalic acid and the corresponding acids having methyl or ethyl groups substituted. The substituted acids may be all of the above substituted by hydroxyl groups, such as glycolic acid, hydroxybutyric acid ($\alpha$, $\beta$ or $\gamma$, respectively), hydroxybenzoic acid with the hydroxy group in the o-, m- or p-position, dihydroxybenzoic acid with the hydroxy groups in 3,4- 2,3- 2,4- 3,5- or 2,5-position; $\alpha$-hydroxy-phenyl-acetic acid.

As phenolic compounds one can, for instance, utilize phenol, $\alpha$- or $\beta$-naphthol, cresol, xylenol, chlorophenol, chlorocresol, chloroxylenol, methylphenols with possibly more than one methyl group, for instance, 2,3,4-trimethylphenol, ethylphenols, propylphenols, butylphenols and the like.

Examples of amines for the reaction of the glycidyl group are, for example, lower alkylamines, di-lower alkylamines, lower alkenylamines, lower di-alkenylamines, cycloalkylamines having 5 to 8 carbon atoms, lower alkyl-cycloalkylamines having 5 to 8 carbon atoms in the cycloalkyl and dicycloalkylamines having 5 to 8 carbon atoms in the cycloalkyl, such as:
methylamine
dimethylamine
ethylamine
diethylamine
n-propylamine
di-n-propylamine
isopropylamine
di-isopropylamine
n-butylamine
di-n-butylamine
sec.-butylamine
di-sec.-butylamine
isobutylamine
di-isobutylamine
tert.-butylamine
n-amylamine
di-n-amylamine
sec.-amylamine
iso-amylamine
di-iso-amylamine
allylamine
di-allylamine
cyclohexylamine
N-methyl-cyclohexylamine
dicyclohexylamine
cyclooctylamine.

Examples of heterocyclic compounds with amino groups are: piperidine, hexamethylenimine, morpholine, as well as aromatic hydrocarbon amines, such as aniline, α-, β-naphthylamine.

The following Examples are illustrative of the practice of the invention without being limitative thereof. In the Examples, the percentage figures given are percent by weight unless otherwise designated.

EXAMPLE 1

Preparation of Diglycidyl-2,3-dihydroxypropyl-isocyanurate 100 gm of triglycidyl isocyanurate were stirred in 1000 ml of pH 7 water at 70° C. for three hours. The remaining, undissolved starting material was filtered off after the solution had cooled off. The solution was then gently evaporated to dryness under an oil pump vacuum. The product mixture contained 9.1% epoxide oxygen and it consisted largely of a mixture of diglycidyl-2,3-dihydroxypropyl isocyanurate and glycidyl-di-(2,3-dihydroxypropyl) isocyanurate.

The mixture was fractionated by means of column chromatography. The column with a diameter of 3 cm was filled with 170 gm of silica gel of a dimension of 0.063 to 0.2 mm. A mixture of methylene chloride/ethyl acetate, 3/2+5% of methanol was used as the mobile phase. Eighteen fractions of 100 ml each were separately isolated, containing a total weight of 38 gm of solids. The fractions 10 to 18 provided 21 gm of the desired compound.

% EpO: 10.3 (theoretical 10.1) (EpO=Epoxide oxygen)
Colorless syrup
Refractive index $n_D^{20}$=1.5093
Mass spectrum and $^1$H-NMR support the structure.

EXAMPLE 2

Preparation of Diglycidyl-2-hydroxy-3-chloropropyl isocyanurate

One mol of cyanuric acid, 60 mols of epichlorohydrin and 0.02 mol of tetraethylammonium bromide were refluxed for three hours. In the course of ¼ to ¾ of an hour after the dissolution of the cyanuric acid, the reaction was complete. The excess epichlorohydrin was distilled off under a water pump vacuum. Then the dichlorohydroxypropane was distilled off under an oil pump vacuum (0.1 mm Hg) while heating on an oil bath (70° C. to 100° C.). This distillation must be made very carefully, since even the smallest amounts of unremoved dichlorohydroxypropane will reduce the yield. Methanol was added to the remaining light-yellow resin and the solution was kept in a refrigerator overnight. Triglycidyl isocyanurate crystallized out with a yield of 35 to 40%. The methanol phase was evaporated at 50° C. under an oil pump vacuum. A mixture of about 70% diglycidyl-2-hydroxy-3-chloropropyl isocyanurate and 20% glycidyl-di(2-hydroxy-3-chloropropyl) isocyanurate was obtained.

Thin-layer chromatogram on silica gel Merck F 60 (Mobile phase: methylene chloride/ethyl acetate 6/4)
RF values:
diglycidyl compound 0.40
monoglycidyl compound 0.27
Analysis values:
8.1% EpO (calculated: 8.2%)
12.1% Cl (Calculated: 12.5%)

The individual components could be purified through column chromatography. The yield of diglycidyl compound amounted to about 30% of a light-yellow, highly viscous liquid.

Epoxide oxygen 9.3% (calculated: 9.6%)
Chlorine content 10.93% (calculated: 10.65%).

EXAMPLE 3

Preparation of Diglycidyl-methyl isocyanurate

1 Mol of methylcyanuric acid (W. J. Close, Journal of the American Chemical Society, 75, 3618 [1953]) was refluxed with 90 mols of epichlorohydrin and 0.1 mol of tetramethylammonium chloride for four hours.

The reaction product was kept under intensive reflux under a vacuum at 40° C. to 50° C. Then 3 mols of NaOH (40% in water) were added slowly, dropwise under stirring and simultaneously the water was continuously azeotropically distilled off. Stirring was continued for another half hour. Then the sodium chloride was filtered off and the solution was reduced to dryness under a vacuum.

The light-yellow resin obtained had an epoxide content of 11.6% (calculated: 12.5%). The structure was confirmed by mass spectrum.

EXAMPLE 4

Preparation of Diglycidyl-(2-hydroxy-3-diethylaminopropyl) isocyanurate 10 gm of α-triglycidyl isocyanurate and 12 gm of diethylamine were dissolved in 250 ml of absolute toluene and heated to 60° C. for six hours under anhydrous conditions. The toluene was then distilled off under a vacuum and 50 ml of methanol were added to the resin-like residue. Overnight the unreacted TGI (about 3 gm)

crystallized out practically completely. The mother liquor was evaporated to dryness and consisted of a mixture of the diglycidyl and monoglycidyl compounds, where the diglycidyl compounds were clearly predominant. The epoxide content of the mixture was 6.8%. The thin-layer chromatogram (silica gel, methylene chloride/ethyl acetate/dimethylamine 55:43:2) after carbonization with sulfuric acid gave two spots.

RF=0.5 diglycidyl compound
RF=0.2 monoglycidyl compound
Intensity ratio 3:1.

The raw product was fractionated through a silica gel column (length 50 cm, diameter 5 cm). Methylene chloride/ethyl acetate 3/2+15% methanol was used as the mobile phase. The mass spectrum and the $^1$H-NMR spectrum support the structure of the isolated diglycidyl-(2-hydroxy-3-diethylaminopropyl) isocyanurate.

EXAMPLE 5

Preparation of Diglycidyl-(2-hydroxy-3-N-morpholinopropyl) isocyanurate 29.7 gm (0.1 mol) of α-triglycidyl isocyanurate and 10 gm of (0.115 mol) of morpholine were treated analogously as in Example 4. Weight of the reaction product mixture: 32 gm. DC (silica gel, mobile phase: methylene chloride/ethyl acetate 3/2).

RF=0.5 diglycidyl compound
RF=0.15 monoglycidyl compound.

The raw substance with a % EpO of 5.8 was fractionated through a silica gel column (length 50 cm, diameter 5 cm).

Mobile phase: methylene chloride/ethyl acetate 3/2+15% methanol

Yield of the diglycidyl compound: 19 gm, pale yellow syrup, % EpO: 8.5 (theoretical value 8.6).

Mass spectrum and $^1$H-NMR spectrum support the structure.

EXAMPLE 6

Preparation of Diglycidyl-[2-hydroxy-3-(2-hydroxyethylthio)propyl-]isocyanurate 20.7 gm (0.1 mol) of α-triglycidyl isocyanurate and 8.0 gm (0.1 mol) of mercaptoethanol as well as 1.5 ml of triethylamine in 500 ml methylene chloride were maintained under reflux for three hours. The reaction mixture was extracted three times with 60 ml each of water, dried with sodium sulfate and subsequently reduced to dryness.

The residue was taken up with 200 ml of methanol and cooled. The crystallized TGI was vacuum filtered off. The methanol phase was reduced to dryness and provided 16 gm of a mixture of mono- and diglycidyl compounds. % EpO: 6.1.

The reaction mixture was separated by means of column chromotography. A column with a 4 cm diameter was filled with 250 gm of silica gel 60. Methylene chloride/ethyl acetate/methanol 3/2/1 was employed as mobile phase.

Yield of the diglycidyl compound: 10.5 gm
% EpO: 8.2 (theoretical value 8.5)
Refractive index $n_N^{20}=1.5207$.

EXAMPLE 7

Preparation of Diglycidyl allyl isocyanurate 20 gm (0.08 mol) of triallyl isocyanurate and 30 gm (0.176 mol) of 3-chloroperoxybenzoic acid in 600 ml of methylene chloride were allowed to stand for 100 hours at 5° C. and 24 hours at room temperature. Then the solution was extracted three times with a sodium carbonate solution and the methylene chloride phase was reduced to dryness.

Yield of the raw product: 26 gm of an oily liquid.

The raw product was taken up in methanol and fractionally crystallized. The first precipitation fraction contains triglycidyl isocyanurate, Mp 70° C. to 115° C. The second precipitation fraction contains 6.4 gm of a reaction product with a Mp of 50° C. to 55° C.

% EpO: 9.0 (theoretical value 11.4)
Iodine number: 143 (theoretical value 90).

This raw reaction product was fractionated via a silica gel column (diameter 5 cm, length 40 cm), which is filled with silica gel 60. Mobile phase: methylene chloride/ethyl acetate 3/2 and the product obtained was crystallized from methanol.

Yield of the diglycidyl compound: 2.4 gm, Mp 57° C. to 60° C.

Iodine number: 102 (theoretical value 90)
Epoxide content: 11.1% (theoretical value 11.4%).

EXAMPLE 8

Preparation of Diglycidyl-(propionyloxy-hydroxy-propyl) isocyanurate 20 gm (0.067 mol) of α-triglycidyl isocyanurate and 50 gm (0.67 mol) of propionic acid in 300 ml of toluene were heated under reflux for 4.5 hours in the presence of 10 gm of molecular sieve 3 Å. The reaction mixture was then filtered and reduced to dryness.

Yield of the raw product: 23.5 gm.

The mixture was taken up into 150 ml of methanol, cooled and the crystallized TGI was vacuum filtered. The methanolic phase was reduced to dryness. After fractionation through a silica gel column, 17.2 gm of a colorless syrup remain.

% EpO: 8.1 (theoretical value 8.2).

Mass spectrum and $^1$H-NMR spectrum support the structure.

EXAMPLE 9

Preparation of Diglycidyl-(2-hydroxy-3-propoxypropyl) isocyanurate 29.7 gm (0.1 mol) of α-triglycidyl isocyanurate and 30 gm (0.5 mol) of n-propanol in 500 ml of toluene were refluxed for six hours. Then the solution was reduced to dryness and taken up into 200 ml of methanol and cooled. The crystallized TGI was vacuum filtered and the methanolic phase was reduced to dryness.

Yield of the reaction raw product: 15 gm of an oily syrup.

The mixture was fractionated by means of column chromatography. The column has a diameter of 5 cm, a length of 50 cm and was filled with 250 gm of silica gel 60. Methylene chloride/ethyl acetate 3/2 was employed as mobile phase.

Yield of diglycidyl compound: 12 gm
% EpO: 8.9 (theoretical value 9.0).

Thin-layer chromatography shows this compound to have a RF value of 0.35 (methylene chloride/ethyl acetate 3/2).

Mass spectrum and $^1$H-NMR confirm the structure.

EXAMPLE 10

Preparation of Diglycidyl-2-hydroxypropyl isocyanurate 5.94 gm (0.02 mol) of α-triglycidyl isocyanurate were dissolved in 200 ml of ethanol/water (7/3). Then 0.76 gm (0.02 mol) of sodium borohydride were added and the reaction mixture was stirred for five hours at room temperature. The turbid solution was acidified with dilute hydrochloric acid, filtered and then extracted three times, each with 200 ml of methylene chloride. The methylene chloride phases were combined, dried over magnesium sulfate and reduced to dryness.

Yield of raw product: 4.8 gm.

% EpO: 8.5 (theoretical value 10.7).

The raw reaction mixture was fractionated by means of a silica gel column. The column had a diameter of 5 cm and a length of 45 cm, and was filled with silica gel 60. Methylene chloride/ethyl acetate/methanol 3/2/1 was employed as the mobile phase.

Yield of diglycidyl compound: 3.7 gm

% EpO: 10.6 (theoretical value 10.7).

In a thin-layer chromatogram with silica gel, the compound has a RF value of 0.45 (methylene chloride-/ethyl acetate/ethanol 3/2/1).

EXAMPLE 11

Preparation of Diglycidyl-2-hydroxy-3-(2',3'-dihydroxypropylthio)-propyl isocyanurate 10 gm (0.034 mol) of triglycidyl isocyanurate, 3.8 gm (0.034 mol) of 1,2-dihydroxy-3-mercaptopropane and 0.1 gm of triethylamine were dissolved or suspended in 200 ml of methanol and stirred for 3.5 hours at 40° C. After gentle distillation of the solvent, 13 gm of a product mixture remained, which was separated by column chromatography with silica gel 60 (Merck) with ethyl acetate/methanol 80/20 as the mobile phase.

Yield of monoadduct: 1.6 gm (11.6%)

% Epoxide oxygen: 7.92 (theoretical value 7.89).

EXAMPLE 12

Preparation of Diglycidyl-2-hydroxy-3-n-octylthio-propyl isocyanurate 10 gm (0.034 mol) of triglycidyl isocyanurate, 5.1 gm (0.034 mol) of n-octylmercaptan and 0.1 gm of triethylamine were dissolved or suspended in 200 ml of methanol and stirred for 3.5 hours at 40° C. After distillation of solvent, there remained 16.1 gm of a product which was separated by column fractionation with silica gel 60 (Merck) and ethyl acetate/methylene chloride/n-hexane 45/45/10 as the mobile phase. 1.4 gm of an 83% product was isolated (7.7% of the theoretical) with 6.21% epoxide oxygen. The structure conforms to the above-mentioned monoadduct.

EXAMPLE 13

Preparation of Diglycidyl-2-hydroxy-3-(benzthiazole-2'-ylthio)-propyl isocyanurate 10 gm (0.034 mol) of triglycidyl isocyanurate, 5.7 gm (0.034 mol) of 2-mercaptobenzthiazole and 0.1 gm of triethylamine were dissolved or suspended in 200 ml of methanol and stirred for 2.5 hours at 40° C. After distillation of solvent, there remained 12.7 gm of a yellowish, solid product, which was separated by column chromatography over silica gel 60 (Merck), and ethyl acetate/-methylene chloride 60/40 as the mobile phase. 2.0 gm of a 92% monoadduct of the above-mentioned structure were isolated (11.4% of theoretical yield); 6.31% epoxide oxygen. The compound was solid and colorless.

EXAMPLE 14

Preparation of Diglycidyl-2-hydroxy-3-(benzimidazol-2'-ylthio)-propyl isocyanurate 10 gm (0.034 mol) of triglycidyl isocyanurate, 5.1 gm (0.034 mol) of 2-mercaptobenzimidazole and 0.1 gm of triethylamine were dissolved or suspended in 200 ml of methanol and stirred for two hours at 40° C. After distillation of solvent, there remained 13.0 gm of a solid product, which was separated by column chromatography with silica gel and ethyl acetate. 1.8 gm of an 89% pure product which was solid and colorless and which possesses an epoxide oxygen value of 6.35% was obtained, being 10.5% of theoretical yield.

EXAMPLE 15

The following experiments were made as per test procedures of the National Cancer Institute, Bethesda, Md., as published in "Cancer Chemotherapy Reports", Part 3, September 1972, Vol. 3, No. 2. The compounds as per the invention were used as the active ingredient. The substances were freshly prepared just prior to application, as aqueous 1% injectable solutions. As per protocol 1200 (page 9 l.c.), tumor type P 388 (Leukemia) was injected i.p. into mice at a value of $10^6$ cells per mouse. The mean survival rate of the thus pretreated animals was determined in a control group (C).

In test groups of animals pretreated in this manner, the effective ingredients, as per the invention, were always given in three doses. Variable amounts of the respective effective ingredient were employed in different experimental series. The average longevity of the respective test group was determined (T). The comparison of mean survival rate of the treated experimental group, as opposed to the untreated control group, gives the extension rate T/C, as a percentage. This extension rate is the extent of effectiveness of the compounds utilized in the experiment. In the following Table the T/C values, corresponding to the concentrations applied of the respective ingredients, are given.

TABLE

| Example | Effective Ingredient Concentration/Dose | TC/ (%) | Repetitions |
|---|---|---|---|
| 3 | 100 | 238 | — |
|   | 50 | 204 |   |
| 7 | 100 | 248 | — |
|   | 50 | 230 | — |
| 5 | 200 | 253 | 303 |
|   | 100 | 196 | 217 |
|   | 50 | 145 | 166 |
|   | 25 | — | 161 |
| 10 | 100 | 250 | — |
|   | 50 | 187 | 226 |
|   | 25 | — | 174 |
|   | 12.5 | — | 167 |
| 1 | 100 | 300 | — |
|   | 50 | 203 | 300 |

TABLE-continued

| Example | Effective Ingredient Concentration/Dose | TC/ (%) | Repetitions |
|---|---|---|---|
| | 25 | — | 197 |
| | 12.5 | — | 174 |
| 8 | 100 | 255 | 269 |
| | 50 | 184 | 216 |
| | 25 | — | 191 |
| | 12.5 | — | 162 |
| 9 | 100 | 213 | 271 |
| | 50 | 184 | 262 |
| | 25 | — | 195 |
| | 12.5 | — | 165 |
| 6 | 100 | 265 | 271 |
| | 50 | 262 | 284 |
| | 25 | — | 298 |
| | 12.5 | — | 192 |
| 4 | 100 | 154 | — |
| | 50 | 164 | — |
| 2 | 100 | 212 | 173 |
| | 50 | 173 | 136 |
| 12 | 200 | 143 | — |
| 11 | 200 | 190 | — |
| | 100 | 151 | — |
| | 50 | 133 | — |
| R =  —CH$_2$—CH—CH$_2$—N(C$_2$H$_4$OH)$_2$ OH | 200 | 167 | — |
| | 100 | 140 | — |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A cytostatic composition consisting essentially of a cytostatically effective amount of at least one N-substituted-diglycidyl-isocyanurate having the formula:

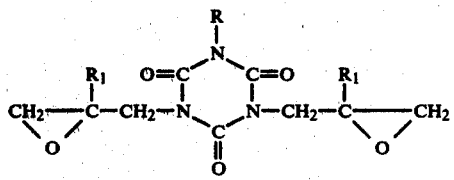

wherein R has from 1 to 15 carbon atoms, which R is a hydrocarbon-containing radical selected from the group consisting of alkyl, aryl, aralkyl, alkaryl, cycloalkyl, and unsaturated derivatives thereof, which R may be further substituted by: heterocycles selected from the group consisting of piperidine, hexamethylenimine, morpholine, benzthiazol-2-ylthio and benzimidazol-2-ylthio, and further substituents on said R selected from the group consisting of halogen, hydroxyl, amino, N-substituted amino having the formula:

—NHR$_2$ and —NR$_2$R$_3$ wherein R$_2$ and R$_3$ together have a total of no more than 8 carbon atoms and are members selected from the group consisting of alkyl and alkyl substituted by hydroxy, halogen and alkoxy, mercapto, alkylmercapto, alkylmercapto substituted by hydroxy, halogen and alkoxy, arylmercapto, alkylsulfoxyl, arylsulfoxyl, alkoxy, aryloxy and alkanoyloxy and aroyloxy, and R$_1$ represents a member selected from the group consisting of hydrogen and alkyl having from 1 to 4 carbon atoms, and a pharmaceutically acceptable carrier therefor.

2. The therapeutic composition of claim 1 wherein R has from 1 to 12 carbon atoms.

3. The therapeutic composition of claim 1 wherein R has from 1 to 8 carbon atoms.

4. The therapeutic composition of claim 1 wherein R has the formula:

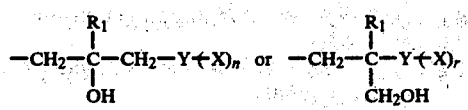

where Y is O, N, S or SO$_2$; X is H, hydroxyl, halogen, lower alkyl, lower alkylol, hydrocarbon aryl and lower alkanoyl; n is an integer of the valence of Y minus 1, and R$_1$ has the above-assigned values.

5. The therapeutic composition of claim 4 wherein R$_1$ is H.

6. The therapeutic composition of claim 1 or 3 wherein R is selected from the group consisting of dihydroxyalkyl, halohydroxyalkyl, N-alkylaminohydroxyalkyl, N-dialkylaminohydroxyalkyl, alkoxyhydroxyalkyl, alkylmercaptohydroxyalkyl, alkylsulfoxyhydroxyalkyl and alkanoyloxyhydroxyalkyl.

7. The therapeutic composition of claim 6 wherein R is selected from the group consisting of dihydroxypropyl, halo-hydroxypropyl, N-alkylamino-hydroxypropyl, N-dialkylamino-hydroxypropyl, alkoxyhydroxypropyl, alkylmercaptohydroxypropyl, alkylsulfoxyhydroxypropyl and alkanoyloxyhydroxypropyl where the hydroxy is in the position selected from the group consisting of the 2 position and the 3 position and the remaining substituent is in the other of the 2 position or the 3 position.

8. A cytostatic method in warm-blooded animals comprising administering a cytostatically effective amount of at least one N-substituted-diglycidyl-isocyanurate having the formula:

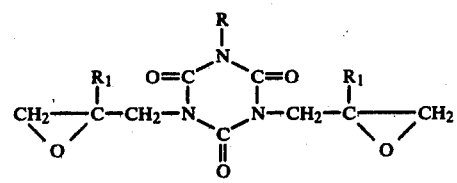

wherein R has from 1 to 15 carbon atoms, which R is a hydrogen-containing radical selected from the group consisting of alkyl, aryl, aralkyl, alkaryl, cycloalkyl, and unsaturated derivatives thereof, which R may be further substituted by: heterocycles selected from the group consisting of piperidine, hexamethylenimine, morpholine, benzthiazol-2-ylthio and benzimidazol-2-ylthio, and further substituents on said R selected from the group consisting of halogen, hydroxyl, amino, N-substituted amino having the formula:

—NHR$_2$ and —NR$_2$R$_3$ wherein R$_2$ and R$_3$ together have a total of no more than 8 carbon atoms and are members selected from the group consisting of alkyl and alkyl substituted by hydroxy, halogen and alkoxy, mercapto, alkylmercapto, alkylmercapto substituted by hydroxy, halogen and alkoxy, arylmercapto, alkylsulfoxyl, arylsulfoxyl, alkoxy, aryloxy and alkanoyloxy and aroyloxy, and $R_1$ represents a member selected from the group consisting of hydrogen and alkyl having from 1 to 4 carbon atom, to a warm-blooded animal.

9. N-substituted-diglycidyl-isocyanurates selected from the group consisting of:
 diglycidyl-(2-hydroxy-3-diethylaminopropyl-)isocyanurate,
 diglycidyl-(2-hydroxy-3-N-morpholinopropyl-)isocyanurate,
 diglycidyl-(2-hydroxy-3-(2-hydroxyethylthio)-propyl)isocyanurate,
 diglycidyl-(propionyloxy-hydroxy-propyl)isocyanurate,
 diglycidyl-(2-hydroxy-3-propoxypropyl)isocyanurate,
 diglycidyl-2-hydroxypropyl isocyanurate,
 diglycidyl-2-hydroxy-3-(2',3'-dihydroxypropylthio)-propyl isocyanurate,
 diglycidyl-2-hydroxy-3-n-octylthiopropyl isocyanurate,
 diglycidyl-2-hydroxy-3-(benzthiazole-2'-ylthio)-propyl isocyanurate, and
 diglycidyl-2-hydroxy-3-(benzimidazol-2'-ylthio)-propyl isocyanurate.

10. The cytostatic composition of claim 1 wherein the N-substituted-diglycidyl-isocyanurate is present in an amount of 0.05 to 5% by weight.

* * * * *

UNITED STATES PATENT AND TRADEMARK OFFICE
CERTIFICATE OF CORRECTION

PATENT NO. : 4,393,060
DATED : July 12, 1983
INVENTOR(S) : HERBERT FISCHER ET AL.

It is certified that error appears in the above-identified patent and that said Letters Patent is hereby corrected as shown below:

Column 5, second last line, change "$SO_2$ or P" to

-- or $SO_2$ --.

Column 22, line 52: "hydrogen-containing" should read

-- hydrocarbon-containing --.

Signed and Sealed this

First Day of May 1984

[SEAL]

Attest:

GERALD J. MOSSINGHOFF

Attesting Officer     Commissioner of Patents and Trademarks